(12) United States Patent
Tsubota et al.

(10) Patent No.: US 8,774,350 B2
(45) Date of Patent: Jul. 8, 2014

(54) X-RAY CT DEVICE

(75) Inventors: Yushi Tsubota, Hitachi (JP); Fumito Watanabe, Kashiwa (JP); Hironori Ueki, Hachioji (JP); Yasutaka Konno, Saitama (JP); Shinichi Kojima, Hitachinaka (JP); Atsuro Suzuki, Hitachi (JP)

(73) Assignee: Hitachi Medical Corporation, Tokyo (JP)

( * ) Notice: Subject to any disclaimer, the term of this patent is extended or adjusted under 35 U.S.C. 154(b) by 276 days.

(21) Appl. No.: 13/391,074

(22) PCT Filed: Aug. 19, 2010

(86) PCT No.: PCT/JP2010/063988
§ 371 (c)(1),
(2), (4) Date: Feb. 17, 2012

(87) PCT Pub. No.: WO2011/036968
PCT Pub. Date: Mar. 31, 2011

(65) Prior Publication Data
US 2012/0170708 A1 Jul. 5, 2012

(30) Foreign Application Priority Data
Sep. 28, 2009 (JP) .................................. 2009-223336

(51) Int. Cl.
*A61B 6/03* (2006.01)
(52) U.S. Cl.
USPC .................................................. 378/7; 378/19
(58) Field of Classification Search
USPC .................................................. 378/7, 16, 19
See application file for complete search history.

(56) References Cited

U.S. PATENT DOCUMENTS

| 5,615,279 | A  | * | 3/1997 | Yoshioka et al. | 378/7 |
| 2008/0226020 | A1 | * | 9/2008 | Proksa | 378/7 |
| 2011/0176663 | A1 | * | 7/2011 | Shaughnessy | 378/207 |
| 2011/0235784 | A1 | * | 9/2011 | Behling | 378/125 |
| 2013/0223588 | A1 | * | 8/2013 | Kurochi et al. | 378/19 |

FOREIGN PATENT DOCUMENTS

| JP | 08-154926 A | 6/1996 |
| JP | 08-252248 A | 10/1996 |
| JP | 10-211199 A | 8/1998 |
| JP | 11-070103 A | 3/1999 |
| JP | 11-089826 A | 4/1999 |
| JP | 2002-320607 A | 11/2002 |

* cited by examiner

*Primary Examiner* — Glen Kao
(74) *Attorney, Agent, or Firm* — Mattingly & Malur, PC

(57) ABSTRACT

Scattered X-rays scattered by an object or a structure enter in a detector (a shift detector) for detecting the positional shift of an X-ray focal point and become a noise source, thereby deteriorating the positional shift detection precision. In particular, the estimation of the dose of scattered X-rays originating from the object is difficult prior to the measurement, and correction of the scattered X-rays is important in order to precisely calculate the positional shift of the X-ray focal point. In order to address this drawback, according to the present invention, a scattered X-ray detector 6 is provided which measures the dose of scattered rays entering in a shift detector 5 for detecting the positional shift of an X-ray focal point 9, and has a function that the output by the shift detector 5 is corrected using the scattered ray dose measured by the scattered X-ray detector.

12 Claims, 12 Drawing Sheets

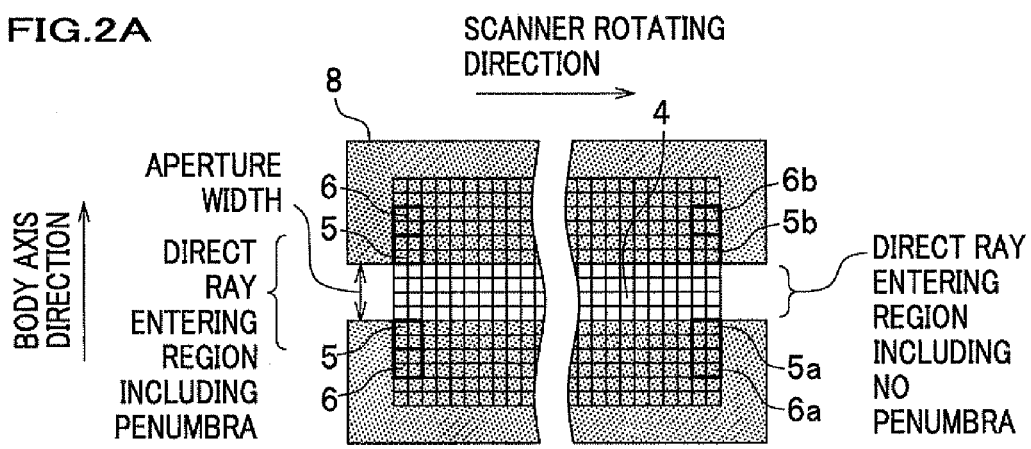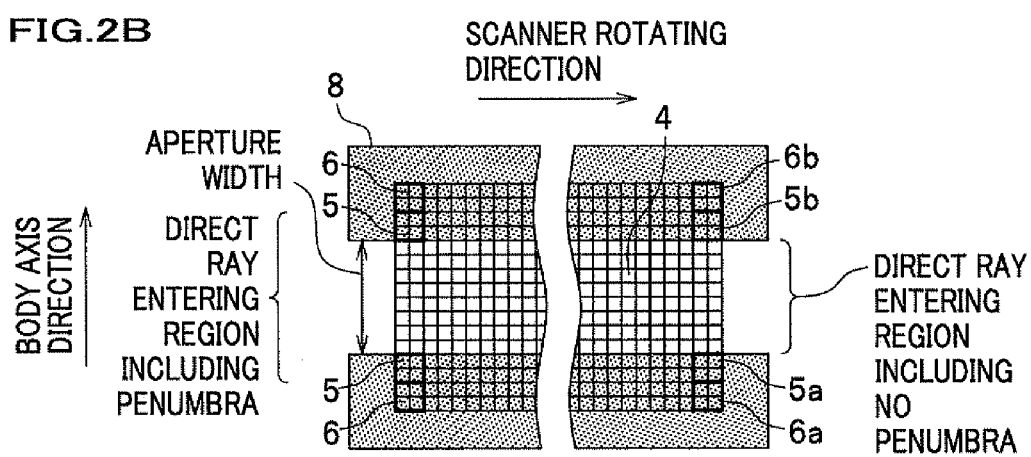

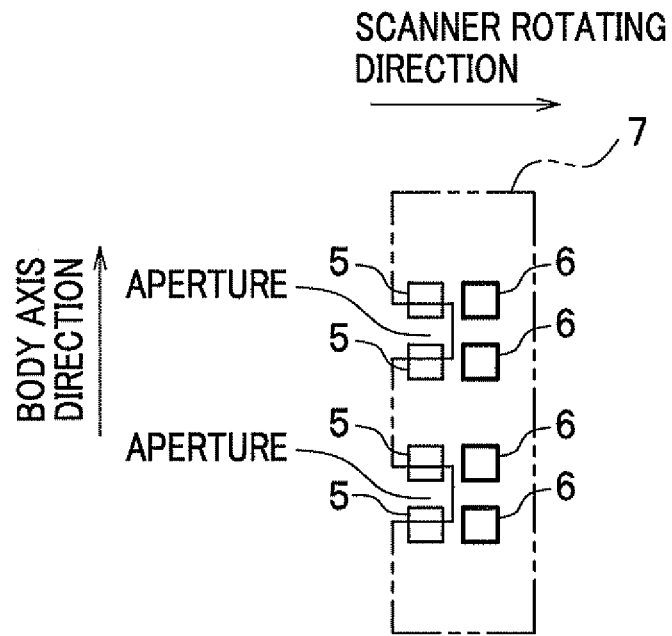
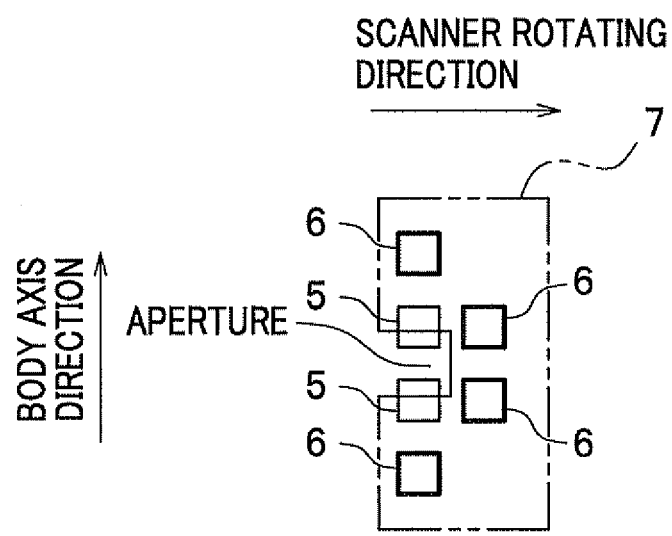

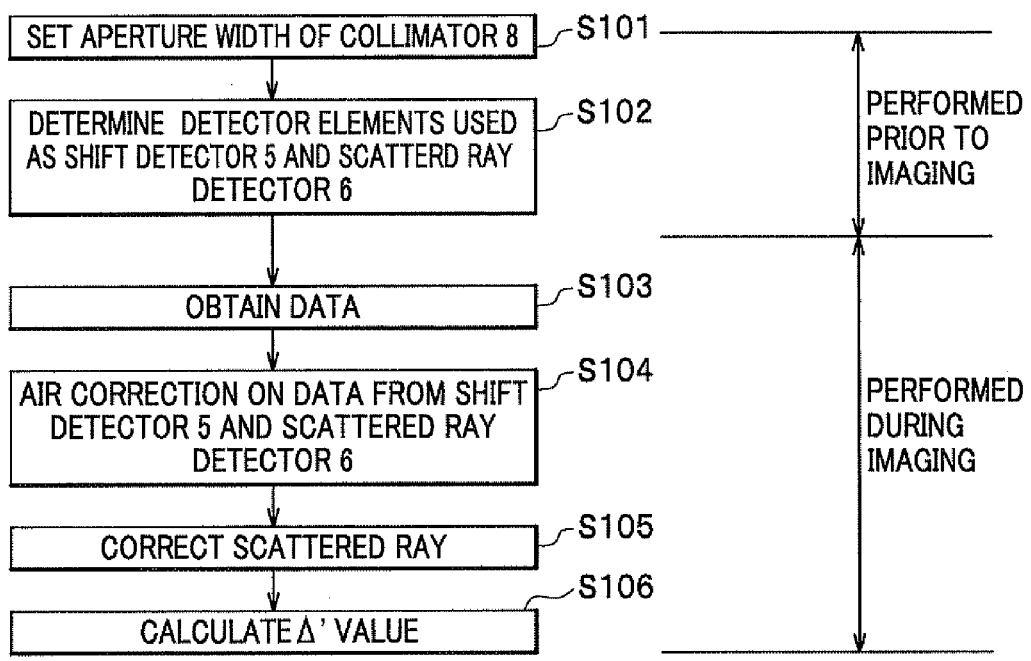
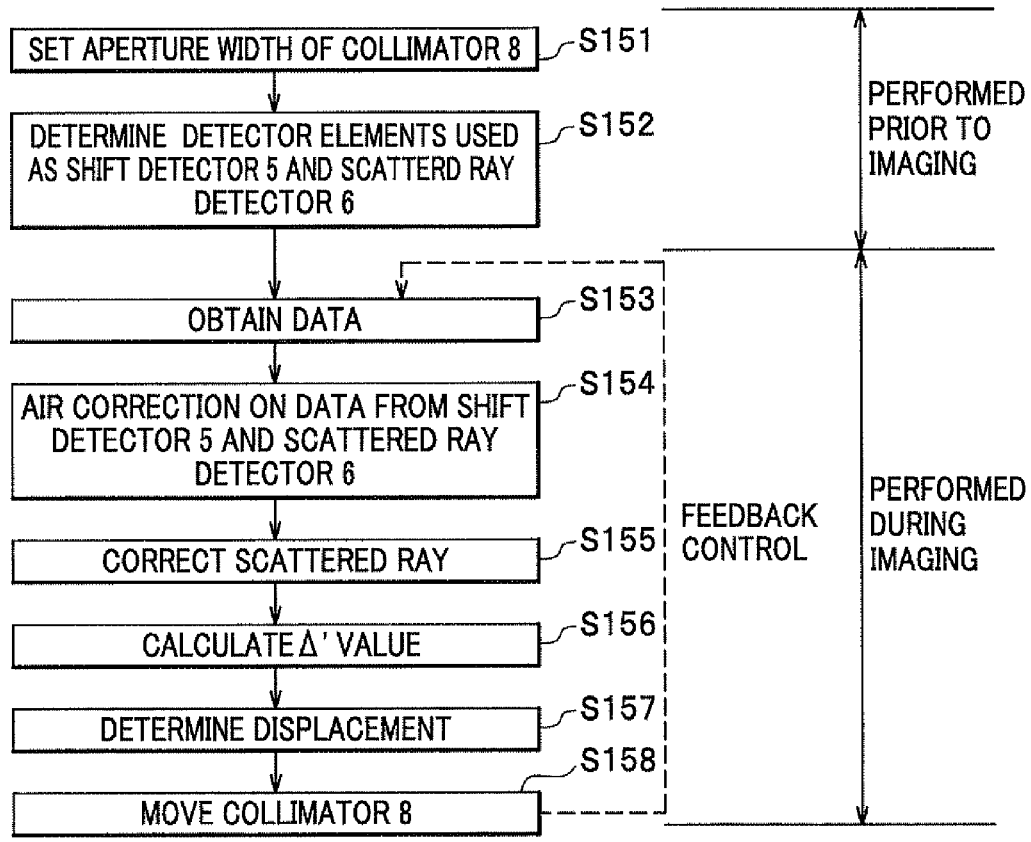

FIG.14
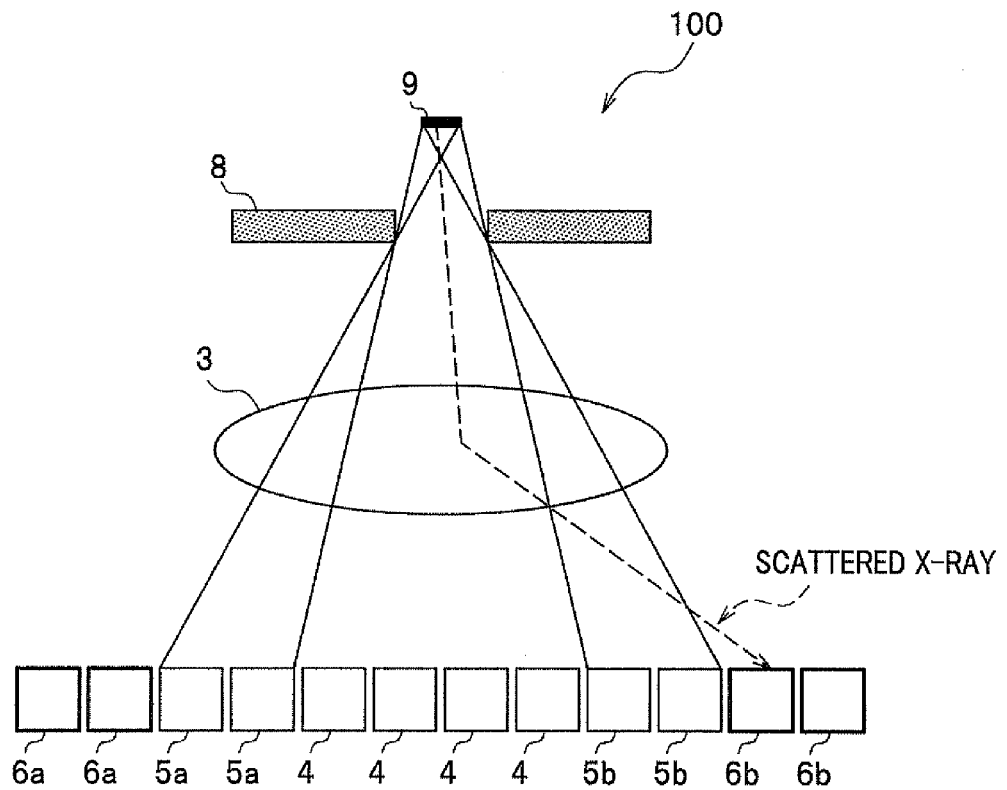
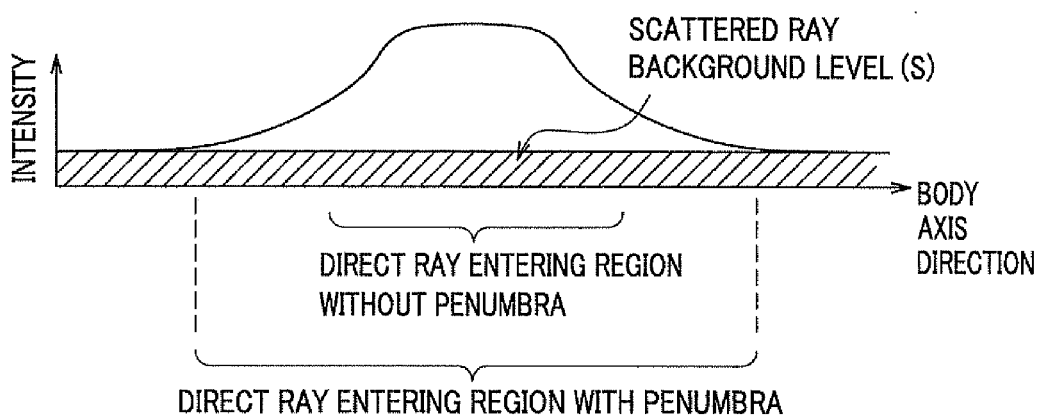

X-RAY CT DEVICE

TECHNICAL FIELD

The present invention relates to an X-ray CT device.

BACKGROUND ART

X-ray CT (Computed Tomography) devices include an X-ray source that irradiates an object with X-rays, and an X-ray detector for imaging an object which is disposed at a position opposite to the X-ray source and for detecting X-rays passing through the object. Such devices reconstruct the differences in the X-ray absorption ratio inside the object as images using a data processing system based on projected data in plural directions obtained by rotational imaging around the object.

In general, the X-ray source uses an X-ray tube that emits electrons accelerated by a high voltage to a positive electrode in order to generate X-rays. However, with respect to the energy used for accelerating the electrons, the generating efficiency of X-rays is low, and most energy is converted into heat. Hence, a phenomenon occurs which shifts the source where X-ray beams are generated due to the thermal expansion of the heated positive electrode.

In order to eliminate the negative effect of such a positional shift of an X-ray focal point and to reduce false images (or artifacts) generated in a reconstructed image, it is necessary to detect the positional shift of the X-ray focal point, and to control the position of the X-ray focal point or to correct measured data.

A detector (hereinafter, referred to as a shift detector) for detecting the positional shift of the X-ray focal point employs a configuration in which equal to or greater than two X-ray detector elements are disposed side by side, and measures the irradiation center of X-rays, i.e., the focal point based on a difference between output signals by respective X-ray detector elements.

Moreover, positional control of the X-ray focal point includes, for example, a method of moving the X-ray tube to the irradiation center or a method of moving a collimator that restricts the X-ray beam range.

Regarding conventional measurement and correction of the positional shift of the X-ray focal point using a shift detector, for example, Patent Literature 1 and Patent Literature 2 disclose X-ray CT devices, respectively. Moreover, regarding a technology of correcting scattered X-rays generated from an object, etc, for example, Patent Literature 3 and Patent Literature 4 disclose a CT scanner and an X-ray CT device, respectively.

PRIOR ART DOCUMENT

Patent Literatures

Patent Literature 1: JP Unexamined Application Publication No. H11-89826 A
Patent Literature 2: JP Unexamined Application Publication No. 2002-320607 A
Patent Literature 3: JP Unexamined Application Publication No. H08-154926 A
Patent Literature 4: JP Unexamined Application Publication No. H08-252248 A

DISCLOSURE OF INVENTION

Problem to be Solved by the Invention

As disclosed in Patent Literature 4 (JP H08-252248 A), scattered X-rays generated by an object or a structural element may enter into the X-ray detector for imaging the object, resulting in a noise source to obtained data.

Likewise, the scattered X-rays entering into the shift detector have the shift detector deteriorate the detection precision on the positional shift of the X-ray focal point.

However, the dose of scattered X-rays changes depending on a size and a shape of the object, which leads to the difficulty in estimating the dose of scattered X-rays derived from the object before the X-ray CT measurement.

Accordingly, an object of the present invention is to correct output by a shift detector in accordance with the dose of scattered X-rays in each measurement and to precisely calculate a positional shift of an X-ray focal point.

Means for Solving the Problem

To achieve the above mentioned object, the present invention provides an X-ray CT device comprising: an X-ray source that emits X-rays from an X-ray focal point; a collimator that collimates the X-rays; a main detector including a plurality of X-ray detector elements disposed in multiple rows to detect X-rays having passed through an object; a focal point shift detector that detects shift of the X-ray focal point; and a scattered ray detector that measures a dose of scattered rays entering in the focal point shift detector.

Effect of the Invention

According to the X-ray CT device of the present invention, the positional shift of an X-ray focal point becomes capable of being calculated precisely using a shift detector.

BRIEF DESCRIPTION OF DRAWINGS

FIGS. 2A and 2B are diagrams showing a configuration of the X-ray CT device according to the first embodiment of the present invention as viewed from an X-ray beam irradiation direction, and showing cases that the respective widths of the collimator apertures are different;

FIG. 8 is a diagram showing a general configuration of the X-ray CT device according to the modified example of the second embodiment of the present invention when a slit has a plurality of apertures;

FIG. 9 is a schematic diagram showing a configuration that the X-ray CT device of the second embodiment of the present invention is combined with the X-ray CT device of the modified example of the second embodiment of the present invention;

FIG. 10 is a flowchart showing a flow of a scattered ray correction process on the data output from a shift detector of the X-ray CT device according to the first embodiment of the present invention;

FIG. 11 is a flowchart showing a flow of the scattered ray correction process and a collimator control on the data output from the shift detector of the X-ray CT device according to the first embodiment of the present invention;

FIG. 14 is a diagram showing a general X-ray intensity profile measured by the shift detector and a scattered X-ray detector in the X-ray CT device according to the first embodiment of the present invention;

BEST MODE FOR CARRYING OUT THE INVENTION

<<First Embodiment>>

An explanation will be given of an X-ray CT device 100 according to a first embodiment of the present invention with reference to FIGS. 1, 2A and 2B.

Figure 1:
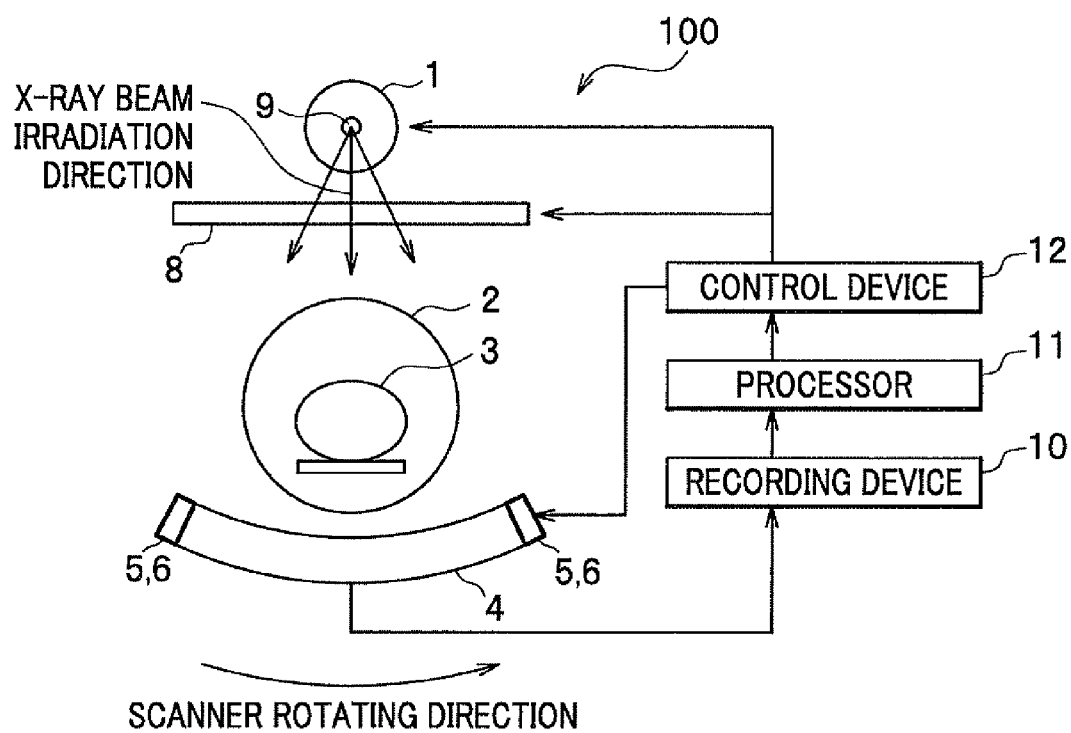
FIG. 1 is a diagram showing a configuration of an X-ray CT device according to a first embodiment of the present invention as viewed from a body axis direction.

FIG. 1 is a diagram showing a configuration of an X-ray CT device according to the first embodiment of the present invention as viewed from a body axis direction. FIGS. 2A and 2B are diagrams each showing a configuration of the X-ray CT device according to the first embodiment of the present invention as viewed from an X-ray beam irradiation direction, and showing cases that the respective widths of the collimator apertures are different.

The X-ray CT device 100 has an unillustrated gantry that is provided at the center thereof with an opening 2 where an object 3 can enter.

The X-ray CT device 100 also has a scanner device that includes an X-ray tube 1 which is an X-ray source, a collimator 8, and an X-ray detector (or a main detector 4) for imaging an object. Those units are supported by the gantry in a rotatable manner around the center of the opening 2 as a central axis of rotation. Such a configuration enables the object 3 inside the opening 2 to be imaged rotationally.

<X-ray Tube 1>

The X-ray tube 1 that is an X-ray source generates X-rays from an X-ray focal point 9 which has a finite dimension inside the X-ray tube 1.

A phenomenon having the positive electrode of the X-ray tube 1 heated and expanded occurs only in a body axis direction (referred to as a slicing direction in some cases), resulting in the shifting of the X-ray focal point 9 only in the body axis direction.

<Collimator 8>

The collimator 8 is disposed between the X-ray tube 1 and the object 3, and adjusts the irradiation range of X-rays so that X-rays are emitted only within a range where an inspection to the object 3 is desired, and thus having a role of avoiding the ineffective exposure of the object 3.

<Main Detector 4>

The X-ray detector for imaging of the object (hereinafter, referred to as the main detector 4) is disposed at a position facing to the X-ray tube 1 with the object 3 placed between the main detector 4 and the X-ray tube 1. The main detector 4 has a plurality of X-ray detector elements disposed in multiple rows in a scanner rotating direction (referred to as a channel direction in some cases) and the body axis direction in order to simultaneously obtain a large number of data on X-ray transmittances through an X-ray irradiation to the object 3 at once.

Herein, the X-ray detector element means the minimum unit that can specify a position of an incident X-ray. For example, in the case of the X-ray detector using scintillators and diodes, an X-ray detection signal is detected by each diode. Hence, the X-ray detector element is a unit of diodes in this case.

<Shift Detector 5>

Shift detectors 5 that detect a shift of the X-ray focal point 9 are disposed at both ends of the main detector 4 in the scanner rotating direction as some of the multiple X-ray detector elements of the main detector 4 so as not to be influenced by the attenuation of X-rays caused by passing of the X-rays through the object 3. Each of the shift detectors 5 uses equal to or greater than two X-ray detector elements arranged side by side in the body axis direction, thereby to measure a difference in penumbra areas set based on the position of the X-ray focal point 9, the size thereof, and the geometric arrangement of the collimator 8. The shift of the X-ray focal point 9 in the body axis direction is calculated based on a measured difference in the penumbra areas.

The term penumbra indicates a condition relating to an irradiation region where X-rays from a part of the X-ray focal point 9 can directly reach but X-rays from other parts of the X-ray focal point 9 cannot directly reach because of a shield, since the X-ray focal point 9 cannot be an ideal point source but has a certain width as a source.

According to the X-ray CT device 100 of the first embodiment, as shown in FIGS. 1 and 2, the shift detectors 5 as a set are disposed at respective ends of the main detector 4 in the scanner rotating direction.

<Scattered X-ray Detector 6>

A scattered X-ray detector 6 is disposed at the external end of each shift detector 5 in the body axis direction in order to estimate the dose of scattered X-rays entering in that shift detector 5.

Herein, a shield is necessary which blocks X-rays so that the X-rays from the X-ray focal point 9 do not directly enter the scattered X-ray detector 6, in order to correctly detect only scattered X-rays.

According to the X-ray CT device 100 of the first embodiment, the collimator 8 adjusts the irradiation range of X-rays, while at the same time, is disposed so that no direct X-rays enter the scattered X-ray detector 6 (see FIG. 14 to be discussed later).

Hence, unlike the shift detector 5, it is necessary to place the scattered X-ray detector 6 sufficiently distant from the shift detector 5 outwardly from the body axis direction so that no penumbra by the collimator 5 overlaps the scattered X-ray detector 6.

Moreover, since the collimator 8 is used as an X-ray shield over the shift detector 5 and the scattered X-ray detector 6, the X-ray detector elements irradiated with X-ray beam or the X-ray detector elements shielded from the X-ray beam have differences depending on the aperture width of the collimator 8. Hence, as shown in FIGS. 2A and 2B, the X-ray detector elements that serve as the shift detector 5 and the scattered X-ray detector 6 are replaced depending on the aperture width of the collimator 8.

In order to improve the statistical accuracy, the X-ray detector elements serving as the shift detector 5 and the scattered X-ray detector 6 may put pieces of data obtained from the plurality of X-ray detector elements together to a piece of the summarized data.

Moreover, in order to eliminate the negative effect by penumbra on the scattered X-ray detector 6, X-ray detector elements may be arranged between the shift detector 5 and the scattered X-ray detector 6; the X-ray detector elements being not used as the shift detector 5 or the scattered X-ray detector 6.

<Positional Shift Correction Process>

Next, will be explained a flow of a correction process for correcting a positional shift of the X-ray focal point 9.

FIG. 10 is a flowchart showing a flow of a scattered ray correction process on data output by the shift detector in the X-ray CT device according to the first embodiment of the present invention.

First, in step S101, prior to imaging, a control device 12 (the X-ray CT device 100) controls the collimator 8 in accordance with an imaging condition of the object 3 set by an operator, and sets the aperture width of the collimator 8.

The control device 12 (the X-ray CT device 100) sets the aperture width of the collimator 8 in such a way that, for example, necessary X-rays can be emitted to the whole concerned area of the object 3. Alternatively, the control device 12 sets the aperture width of the collimator 8 in such a way that X-rays are directly emitted to the whole area of the X-ray focal point 9 up to the periphery of the concerned area of the object 3, while regions outside the concerned area are not directly irradiated with the X-rays as less as possible, in order to reduce the ineffective exposure.

Next, in step S102, a processor 11 (the X-ray CT device 100) sets the X-ray detector elements to be the main detector 4, the shift detectors 5, and the scattered X-ray detectors 6 in accordance with the position of the X-ray focal point 9, the size thereof, the position of the collimator 8, the aperture width thereof, and the geometric arrangement of the X-ray detector elements.

FIG. 14 shows a relationship between a position of the X-ray detector element in the body axis direction and a signal intensity.

More specifically, FIG. 14 is a schematic diagram showing a general profile of an X-ray intensity measured by the shift detector and the scattered X-ray detector in the X-ray CT device according to the first embodiment of the present invention.

First, will be explained the geometric arrangement of the X-ray focal point 9, the collimator 8, the main detector 4, the shift detector 5, and the scattered X-ray detector 6 with reference to FIG. 14.

Since the X-ray focal point 9 is not an ideal point source but has a width as a source, there are regions comprising: a region (or a direct X-ray region including no penumbra) where X-rays directly enter from the whole area of the X-ray focal point 9; a penumbra region where X-ray can directly reach from a part of the X-ray focal point 9 but the X-rays cannot directly reach from the other parts of the X-ray focal point 9 due to the shield (or the collimator 8); and a region where no X-rays directly enter from the X-ray focal point 9 due to the shield (or the collimator 8). As shown in FIG. 14, those regions are set geometrically in accordance with the position of the X-ray focal point 9, the size thereof, the position of the collimator 8, the aperture width thereof, and the arrangement of the X-ray detector elements.

Regarding the X-ray detector elements, the main detector 4 is generally disposed in the direct X-ray region which includes no penumbra. Moreover, the shift detector 5 is disposed in the penumbra region. Furthermore, the scattered X-ray detector 6 is disposed in the region where no X-rays directly enter from the X-ray focal point 9 to measure only scattered rays which are not influenced by the penumbra.

However, the aperture width of the collimator 8 may be narrowed to reduce the range of the radiation exposure, and the main detector 4 may be disposed so that a part of the penumbra region overlaps the main detector 4. In such a case, a single X-ray detector element may serve as both main detector 4 and shift detector 5.

On the other hand, the shift detector 5 may be disposed so that the direct X-ray region having no penumbra overlaps a part of the shift detector 5 or so that the region where no X-rays directly reach from the X-ray focal point 9 overlaps a part of the shift detector 5.

Conversely, the scattered X-ray detector 6 measures only scattered rays which are not influenced by the penumbra, thereby to be disposed so that no penumbra region overlaps the scattered X-ray detector 6.

In the case of FIG. 14, X-ray detector elements 5a and 5b in the penumbra region are set as the shift detectors 5. Moreover, X-ray detector elements 6a and 6b, in which no X-rays from the X-ray focal point 9 directly enter since those X-rays are blocked by the collimator 8, while the scattered X-rays generated by the object 3 or the like enter, are set as the scattered X-ray detectors 6.

<Imaging>

Next, with reference to FIG. 10 again, will be explained the rest of the correction process in the positional shift of the X-ray focal point 9.

After the X-ray detector elements used as the shift detectors 5 and the scattered X-ray detectors 6 are set (step S102), the X-ray CT device 100 proceeds to the next step of imaging the object 3.

During the imaging, X-rays are generated at the position of the X-ray focal point 9, and the collimator 8 adjusts the X-ray irradiation range.

The X-rays having passed through the object 3 are detected by the main detector 4, and signals in accordance with the X-ray intensity are transmitted as the data to the data processing system (a recording device 10, the processor 11, and the control device 12) (see FIG. 1) of the X-ray CT device 100, thereby to be converted to images.

At this time, the data processing system (the recording device 10, the processor 11, and the control device 12) of the X-ray CT device 100 simultaneously obtains data from the shift detectors 5 and the scattered X-ray detectors 6 (step S103).

<Focal Point Shifted Level Determination>

The shifted level of the X-ray focal point 9 is determined based on the data obtained from the shift detectors 5 and the scattered X-ray detectors 6 (steps S103 to S106).

A method for determining the shifted level of the X-ray focal point 9 will be explained below.

In step S104, the processor 11 reads out data (or air data) imaged in the condition without object 3 stored in the recording device 10 in advance from the recording device 10, and standardizes data obtained from the shift detectors 5 and the scattered X-ray detectors 6 with the air data, thereby performing a correction process (or air correction) of correcting the sensitivity deviation among the X-ray detector elements.

Next, when the shift detector 5 is configured by equal to or greater than two X-ray detector elements, as indicated by the reference numerals 5a and 5b in FIG. 14, after conducting the air correction, are averaged data of the X-ray detector elements 5a located at the left side of the body axis with respect to the main detector 4. Likewise, after conducting the air correction, are also averaged data of the X-ray detector elements 5b located at the right side of the body axis.

Hereinafter, the value of averaged data obtained from the X-ray detector elements 5a in FIG. 14 is denoted by a reference symbol A, and the value of averaged data obtained from the X-ray detector elements 5b in FIG. 14 is denoted by a reference symbol B.

When the scattered X-ray detector 6 is configured by equal to or greater than two X-ray detector elements, as indicated by the reference numerals 6a and 6b in FIG. 14, after conducting the air correction, are averaged data of the X-ray detector elements 6a located at the left side of the body axis with respect to the main body detector 4. Likewise, after conducting the air correction, are averaged data of the X-ray detector elements 6b located at the right side of the body axis.

Hereinafter, the value of averaged data obtained from the X-ray detector elements 6a in FIG. 14 is denoted by a reference symbol C, and the value of averaged data obtained from the X-ray detector elements 6b in FIG. 14 is denoted by a reference symbol D. The reference numerals 5a, 5b, 6a, and 6b in FIG. 14 denote the X-ray detector elements at both ends in the scanner rotating direction.

In the X-ray CT device 100 that rotationally picks up images, by utilizing data picked up in different scanner rotating angles (or views) the statistical accuracy of the scattered ray detection may be improved. More specifically, provided that the scattered ray distribution is gently-sloping, values of adjacent view data may be averaged.

Moreover, in the case of helical scanning, may be averaged data measured by the scattered X-ray detector 6 at the end of the right side of the body axis in a certain scanner rotating angle (or view) and data measured by the scattered X-ray detector 6 at the end of the left side of the body axis in a scanner rotating angle (or view) after the scanner is rotated. Hereby, the averaged data allows the statistical accuracy to be improved.

Furthermore, in the case of a normal scanning having the irradiation range to the object 3 not advanced in the body axis direction, even if the scanner rotates, by averaging the outputs by the scattered X-ray detectors 6 before and after a rotation, the statistical accuracy may also be improved. In this case, the more the number of scanner rotations is, the more the statistical accuracy improves.

Next, will be explained a method of calculating the positional shift of the X-ray focal point 9 in steps S105 and S106.

$\Delta$ that represents the position shifted level of the X-ray focal point 9 is defined in the form of (formula 1) below.

$$\Delta = 2 \times (A-B)/(A+B) \quad \text{(Formula 1)}$$

When, however, the shift detectors 5 are disposed at respective ends of the main detector 4, as shown in FIG. 14, in practice, A and B unavoidably include the scattered X-rays that change in a real time manner from the object 3, etc, as a scattered ray background level S. When this scattered ray background level S is clarified, A and B can be expressed as the followings (formula 2) and (formula 3), respectively. Note that a symbol ' indicates that no scattered X-ray is included.

$$A = A' + S_{(5(a))} \quad \text{(Formula 2)}$$

$$B = B' + S_{(5(b))} \quad \text{(Formula 3)}$$

Provided that the scattered ray distribution is gently-sloping in the body axis direction, using data having conducted the air correction and obtained from the scattered X-ray detectors 6, approximation in zero-order is performed. If the values of A and B are subjected to the scattered ray correction, the followings (formula 4) and (formula 5) can be obtained (step S105).

$$A' = A - C \quad \text{(Formula 4)}$$

$$B' = B - D \quad \text{(Formula 5)}$$

Using A' and B' having conducted the scattered ray correction, $\Delta'$ that represents the positional shift level of the X-ray focal point 9 may be calculated through the following (formula 6) (step S106).

$$\Delta' = 2 \times (A' - B')/(A' + B') \quad \text{(Formula 6)}$$
$$= 2 \times (A - B - C + D)/(A + B - C - D)$$

According to the X-ray CT device 100 in the first embodiment of the present invention, the following advantages may be obtained.

(First Advantage)

The negative effect by the scattered X-rays, in particular, the scattered X-rays from the object 3, which change in every measurement, may be corrected and eliminated using the above-explained $\Delta'$ value, and thus the positional shift of the X-ray focal point 9 may be calculated precisely.

(Second Advantage)

The penumbra region important for detecting the positional shift of the X-ray focal point 9, and the region that no direct X-ray enters and needs detecting the scattered rays are separately defined from each other. Herein, data obtained from the X-ray detector elements disposed in the respective regions at appropriate positions are added and combined together as needed, resulting in the improvement of the detection precision in the positional shift of the X-ray focal point 9.

(Third Advantage)

The shift detectors 5 and the scattered X-ray detectors 6 are formed as some of the X-ray detector elements of the main detector 4, which reduces the cost if the shift detectors 5 and the scattered X-ray detectors 6 are separately formed, and also reduces the maintenance effort like layout adjustment.

The collimator 8 may be controlled as follows based on the focal point data obtained through the above mentioned process.

The irradiation range of X-rays entering into the main detector 4 becomes adjustable by controlling the collimator 8 in a real time manner during the imaging process in accordance with the positional shift of the X-ray focal point changing from moment to moment. The focal point data may be utilized to enable more precise adjustment.

<Collimator 8 Control>

Next, will be explained a flow of the correction process in the positional shift of the X-ray focal point 9 and a flow of the control of the collimator 8 with reference to FIG. 11.

FIG. 11 is a flowchart showing a flow of a scattered ray correction process and a collimator control on data obtained from the shift detector in the X-ray CT device according to the first embodiment of the present invention.

The flow from step S151 to step S156 is the same as the flow from the step S101 to the step S106 shown in FIG. 10, and the duplicated explanation thereof will be omitted. Note steps S151, S152, S153, S154, S155, and S156 correspond to the steps S101, S102, S103, S104, S105, and S106, respectively.

In the step S157, the processor 11 determines the shift of the collimator 8 from the Δ' value obtained in the step S156.

The shift of the collimator 8 may be determined by, for example, multiplying the Δ' value by a proportional constant most appropriate for a scanning condition measured in advance.

In the step S158, the control device 12 shifts the position of the collimator 8 through a feedback circuit, thereby moving the position of the penumbra.

A control method of the X-ray irradiation range using the feedback circuit will be explained below.

When, for example, each of X-ray detector elements 5a and the X-ray detector elements 5b shown in FIG. 14 is disposed with an identical distance apart from the visual field center of the body axis in the right and left directions, the X-ray focal point 9 where Δ' calculated from each output signal satisfies a condition that Δ'=0 is the center of the X-ray irradiation range in the body axis direction.

Hence, when Δ' obtained through the above-explained method has a positive value, the collimator 8 is moved to the X-ray detector element side, which has obtained the output B, and when Δ' has a negative value, the collimator 8 is moved to the X-ray detector element side, which has obtained the output A. This may overcome a problem that the X-ray irradiation range is misaligned with the main detector 4 due to the positional shift of the X-ray focal point 9 while suppressing an ineffective radiation exposure to the object 3.

By moving the collimator 8, the value of Δ' dynamically changes during the imaging, and is controlled so that Δ' becomes zero, and thus the estimation precision of the most appropriate proportional constant may be improved. This enables quick and precise control of the X-ray irradiation range.

Here, when the shift detector 5 causes the phenomenon (hereinafter, referred to as "object overlap") such as attenuation of signals, it is appropriate not to use the value of Δ' at this moment. Such a phenomenon occurs due to the positioning of the object 3 between X-ray focal point 9 and the shift detector 5 in the case of imaging the large object 3 or an off-center imaging that images the object 3 having the body axis thereof shifted relative to the scanner rotating direction, Further, when all the shift detectors 5 cause the object overlap phenomenon, it is appropriate not to control the collimator 8 at this moment.

Conversely, regarding the X-ray detector elements having no object overlap phenomenon in the body axis direction, all X-ray detector elements may be used as the shift detectors 5 and the scattered X-ray detectors 6. This may increase the statistic quantity, thereby improving the statistical accuracy.

The object overlap is determined based on, for example, whether or not a dose is equal to or smaller than an appropriate threshold regarding data of the X-ray detector element of the main detector 4 located inwardly of the shift detector 5 and having conducted a reference correction. The threshold varies depending on the required determination precision.

The reference correction is a process of correcting a gain change typical of a voltage fluctuation of the X-ray tube 1 at the time of obtaining the air data and at the time of imaging the object 3.

This may be carried out by standardizing measured data of each sliced row (the row of X-ray detector elements arranged side by side in the scanner rotating direction) by data (both-end average) measured by the X-ray detector elements at both ends of the main detector 4 in the scanner rotating direction which can detect direct X-rays not penetrating the object 3. However, within a range in which the gain change for each sliced row is ignorable, reference correction may be performed using the average value of data of detector elements located at the ends of respective sliced rows.

In the X-ray CT device 100 according to the first embodiment of the present invention, in addition to the above-explained (first advantage), (second advantage), and (third advantage), the following advantages can be further obtained by performing the collimator-8 control process.

(Fourth Advantage)

By using the above-explained Δ' value, the negative effect of scattered X-rays, in particular, scattered X-rays from the object 3 changing for each measurement can be corrected and eliminated, and thus the positional shift of the X-ray focal point 9 may be further precisely calculated. This results in quick and precise control of the X-ray irradiation range, ensuring a real-time control.

(Fifth Advantage)

When the averages of respective signals from 5a and 5b in FIG. 14 are set to be the same value and a feedback control is performed with Δ'=0, the moving direction may be determined based on only the positive/negative value of Δ' (i.e., negative feedback). Accordingly, the collimator control circuit may be simplified.

<<Second Embodiment>>

In the first embodiment, the collimator 8 that is the shield against X-rays is used, but the X-ray detector elements used as the shift detectors 5 and the scattered X-ray detectors 6 are ones located at merely both ends in the scanner rotating direction among the X-ray detector elements shielded by the collimator 8.

In order to utilize the X-ray detector elements as the main detector 4 more effectively, the following second embodiment is advantageous, which has a separate shield.

Figure 3:
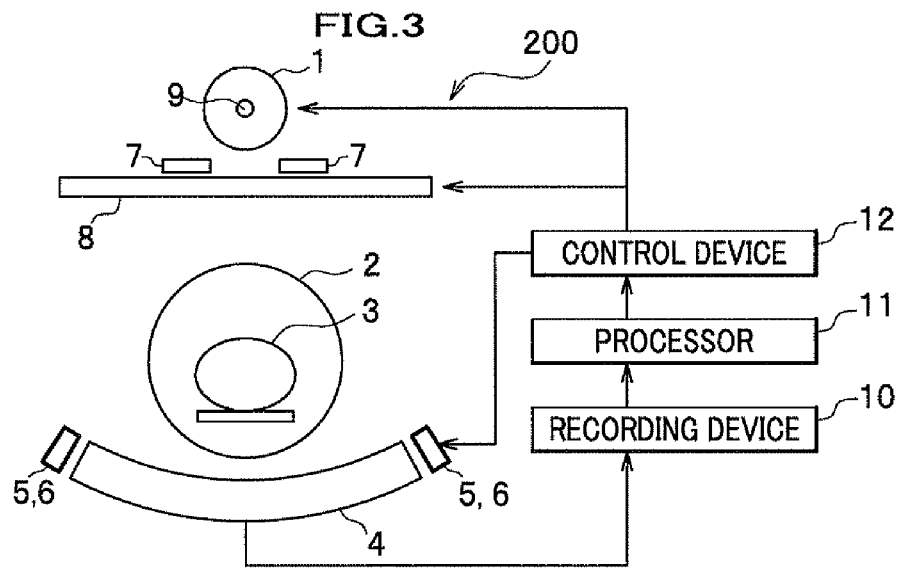
FIG. 3 is a diagram showing a configuration of an X-ray CT device according to a second embodiment of the present invention as viewed from a body axis direction.
Figure 4:
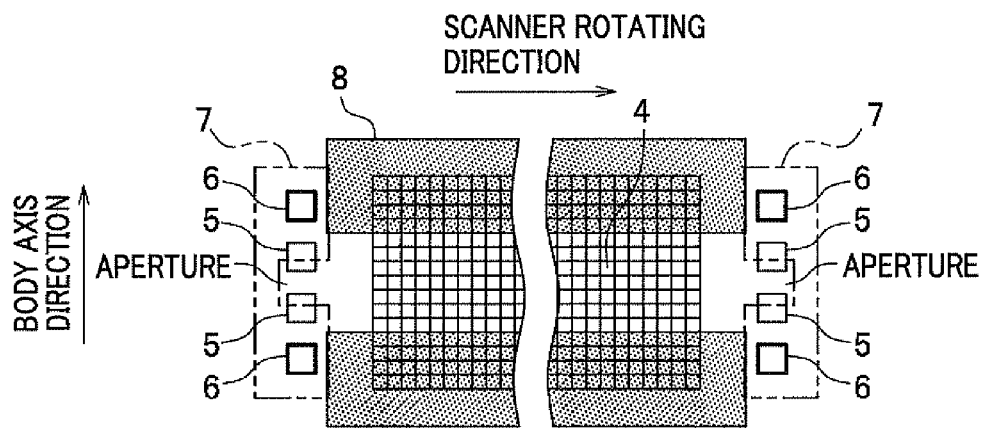
FIG. 4 is a diagram showing a configuration of the X-ray CT device according to the second embodiment of the present invention as viewed from an X-ray beam irradiation direction.

FIGS. 3 and 4 show an X-ray CT device 200 according to the second embodiment of the present invention.

FIG. 3 is a diagram showing a configuration of the X-ray CT device according to the second embodiment of the present invention as viewed from a body axis direction, and FIG. 4 is a diagram showing a configuration of the X-ray CT device according to the second embodiment of the present invention as viewed from the X-ray beam irradiation direction.

The basic configuration is consistent with that of the X-ray CT device 100 according to the first embodiment, and the same element will be denoted by the same reference numeral in order to eliminate the duplicated explanation.

However, according to the X-ray CT device 200 of the second embodiment, slits 7 which are new X-ray shields each having an aperture allowing the X-rays to pass through at the center thereof in the body axis direction are provided between the X-ray focal point 9 and the shift detectors 5 and the scattered X-ray detectors 6. Moreover, the shift detectors 5 and the scattered X-ray detectors 6 are separately provided from the main detector 4.

The shift detector 5 measures, by equal to or greater than two X-ray detector elements arranged side by side in the body axis direction, a difference in penumbra areas set in accordance with the position of the X-ray focal point 9, the size thereof, and the geometric arrangement of the slits 7, thereby calculating the shift Δ' of the X-ray focal point 9 in the body axis direction.

The scattered X-ray detector 6 is disposed at the external end of the shift detector 5 in the body axis direction in order to estimate the dose of scattered X-rays entering in the shift detector 5. The scattered X-ray detector 6 needs an X-ray shield so that no direct X-ray enter in the scattered X-ray detector 6, and the X-ray CT device 200 of the second embodiment has the slits 7 as the shield.

Unlike the shift detector 5, it is necessary to dispose the scattered X-ray detector 6 sufficiently distant from the shift detector 5 outwardly of the body axis direction so that no penumbra by the slit 7 overlaps the scattered X-ray detector 6. Alternatively, the shift detector 5 needs to include X-ray detector elements having a sufficiently large size outwardly of the body axis direction or a sufficiently large number of X-ray detector elements in that direction.

The shift detectors 5 and the scattered X-ray detectors 6 are separately provided from the main detector 4 as explained above, and thus the X-ray detector elements serving as the shift detectors 5 and the scattered X-ray detectors 6 are always consistent regardless of the aperture width of the collimator 8.

Moreover, the shift detector 5 and the scattered X-ray detector 6 may be disposed at only one end of the main detector 4 in the scanner rotating direction.

Figure 5:
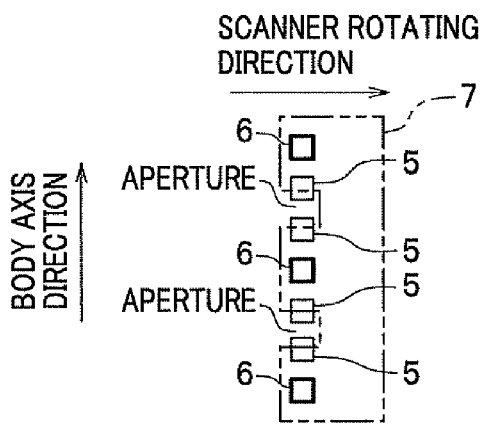
FIG. 5 is a schematic diagram showing a configuration of the X-ray CT device according to the second embodiment of the present invention when a slit has a plurality of apertures.

FIG. 5 is a diagram showing a general configuration of the X-ray CT device according to the second embodiment of the present invention when the slit has a plurality of apertures.

As shown in FIG. 5, a devisal may be made which has the slit 7 provided with a plurality of apertures to improve the statistical accuracy.

The shift detector 5, the scattered X-ray detector 6 and the main detector 4 shown in FIGS. 3, 4, and 5 may be disposed so as to adjoin to one another.

In order to improve the statistical accuracy, a plurality of X-ray detector elements serving as the shift detector 5 and the scattered X-ray detector 6 may be provided and pieces of data obtained from those X-ray detector elements may be combined together as single data.

In the case of FIG. 3, the slits 7 are disposed between the X-ray focal point 9 and the collimator 8, it is appropriate if such slits 7 are disposed at respective positions where the dose of incident scattered X-rays into the shift detector 5 and that of incident scattered X-rays into the scattered X-ray detector 6 become substantially equal, X-rays directly entering in the main detector 4 are not interrupted, but X-rays directly entering in the scattered X-ray detector 6 are blocked, and the slits 7 do not interfere with the object 3 when entering in the opening 2.

Next, with reference to FIGS. 12 and 15, will be explained a flow of a correction process of the positional data on the X-ray focal point 9.

Figure 12:
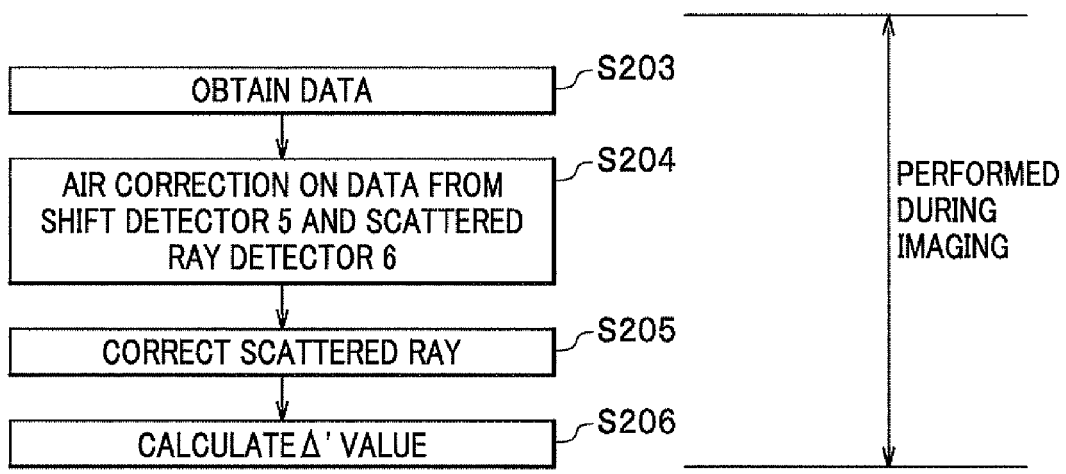
FIG. 12 is a flowchart showing a scattered ray correction process on the data output from a shift detector of the X-ray CT device according to the second embodiment of the present invention.

FIG. 12 is a flowchart showing a flow of a scattered ray correction process and a collimator control relating to data from the shift detector in the X-ray CT device according to the second embodiment of the present invention. FIG. 15 is a schematic diagram showing a general profile of X-ray intensity measured by the shift detector and the scattered X-ray detector.

Figure 15:
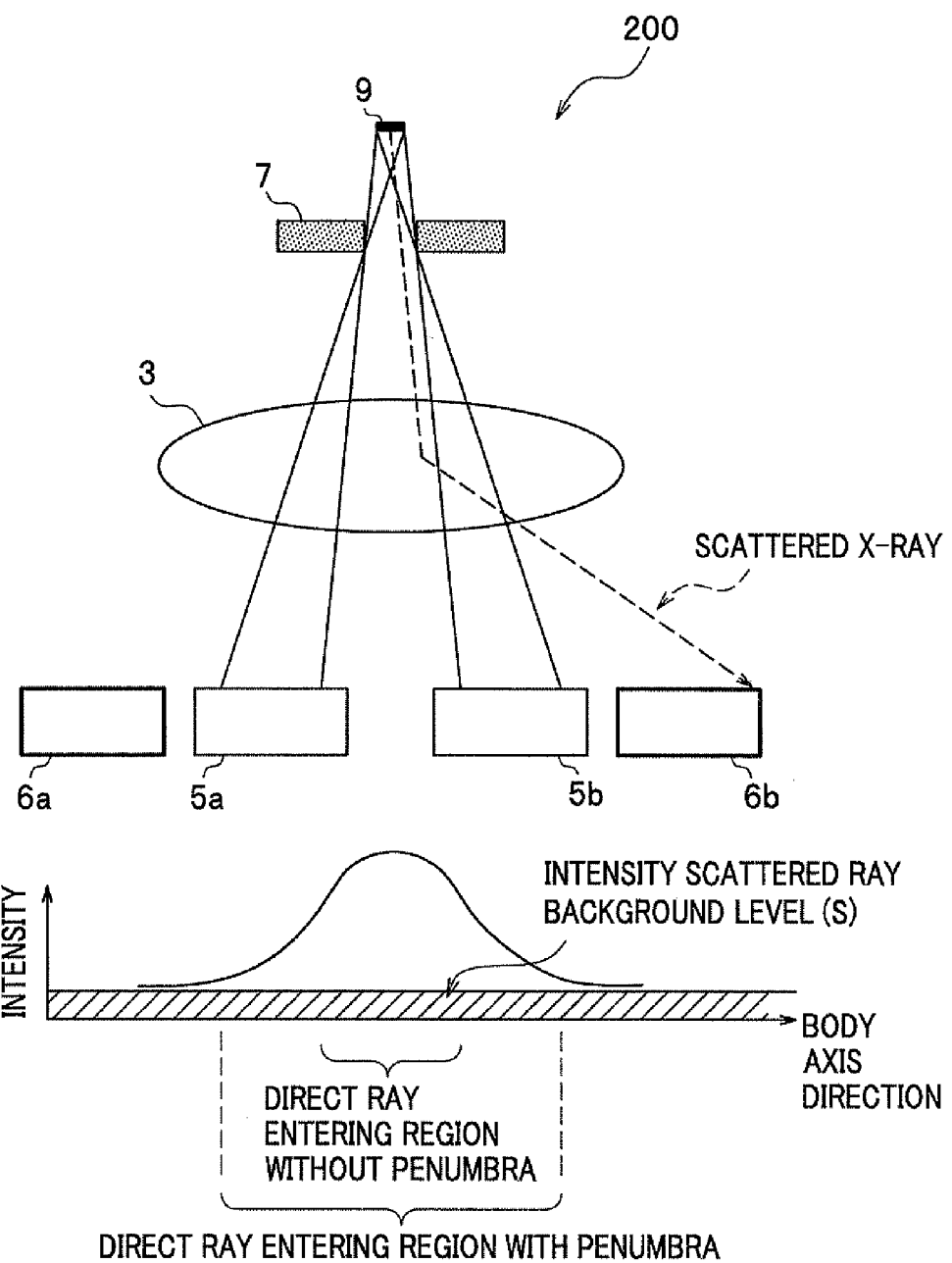
FIG. 15 is a diagram showing a general X-ray intensity profile measured by the shift detector and a scattered X-ray detector in the X-ray CT device according to the second embodiment of the present invention.

The basic flow and configuration are similar to those of the first embodiment, and FIGS. 10 and 14 can be observed in place of FIGS. 12 and 15, respectively.

Moreover, steps S203, S204, S205, and S206 correspond to steps S103, S104, S105, and S106, respectively.

However, according to the X-ray CT device 100 of the first embodiment, depending on the aperture width of the collimator 8, the X-ray detector elements serving as the shift detector 5 and the scattered X-ray detector 6 differ, and thus the X-ray detector elements used as the shift detector 5 and the scattered X-ray detector 6 are set in each measurement (see steps S101 and S102 in FIG. 10). According to the X-ray CT device 200 of the second embodiment, the X-ray detector elements used as the shift detector 5 and the scattered X-ray detector 6 are predefined, and thus a process of setting the X-ray detector elements to be used as the shift detector 5 and the scattered X-ray detector 6 is omitted.

Moreover, as shown in FIG. 5, when the slit 7 is provided with a plurality of apertures, regarding the shift detector 5 disposed between the plurality of scattered X-ray detectors 6, correction can be performed on such a shift detector 5 with a first order or second order scattered ray background presumed in advance.

According to the X-ray CT device of the second embodiment, in addition to the (first advantage) and (second advantage) of the X-ray CT device 100 in the first embodiment, the following advantages may be obtained.

(Sixth Advantage)

Constant data control is enabled regardless of the aperture width of the collimator 8.

(Seventh Advantage)

Since the X-ray detector elements used as the shift detector 5 and the scattered X-ray detector 6 are separately provided, the number of X-ray detector elements not to be used may be minimized. That is, the sliced rows at the ends of the main detector 4 may be maximally utilized for imaging the object 3.

The collimator 8 may be controlled using data on the positional shift of the X-ray focal point 9 like the first embodiment.

Next, will be explained a flow of a correction process of the positional shift of the X-ray focal point and the collimator-8 control with reference to FIG. 13.

Figure 13:
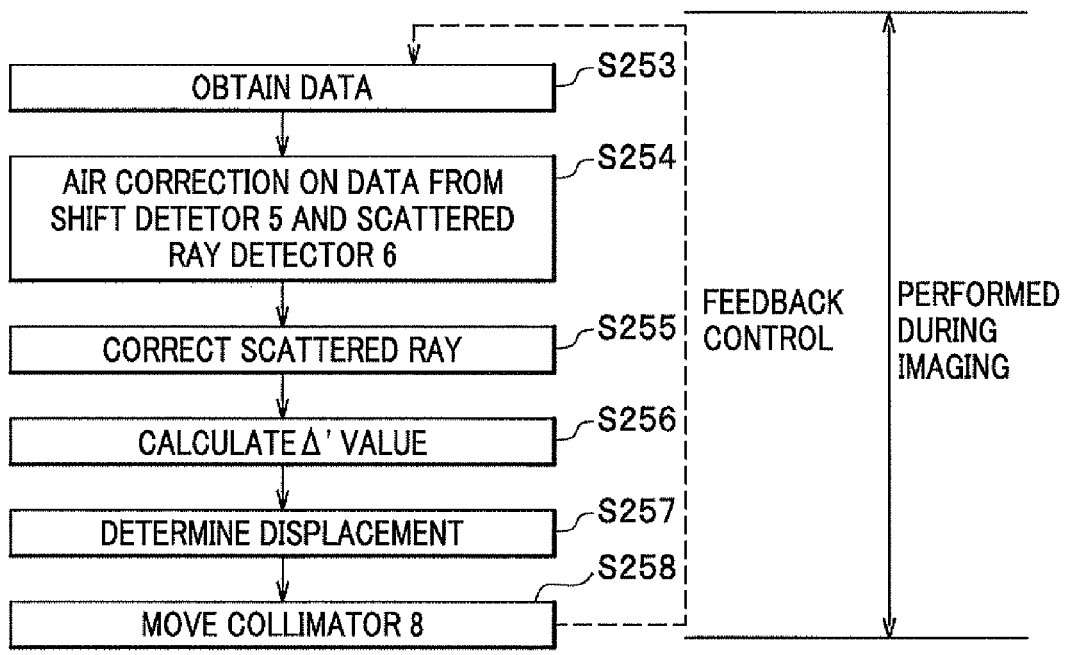
FIG. 13 is a flowchart showing a flow of the scattered ray correction process and a collimator control on the data output from the shift detector of the X-ray CT device according to the second embodiment of the present invention.

FIG. 13 is a flowchart showing a flow of a scattered ray correction process and a collimator control on data output by the shift detector in the X-ray CT device according to the second embodiment of the present invention.

A flow from step S253 to step S256 is consistent with the flow from the step S203 to the step S206 shown in FIG. 12, and the flow from step S257 to step S258 are similar to the flow shown in FIG. 11. Thus, the duplicated explanation will be omitted. Herein, the steps S253, S254, S255, S256, S257, and S258 correspond to the steps S203, S204, S205, S206, S157, and S158, respectively.

However, the slits 7 of the X-ray CT device 200 of the second embodiment move in synchronization with the control for the collimator 8, and are disposed so that the aperture center of the slit 7 in the body axis direction always matches the aperture center of the collimator 8.

The X-ray CT device 100 of the first embodiment and the X-ray CT device 200 of the second embodiment can perform feedback control on the X-ray irradiation range by moving the X-ray tube 1 and the main detector 4 (including the shift detectors 5 and the scattered X-ray detectors 6) instead of controlling the collimator 8 by the control device 12. In this case, the slits 7 of the X-ray CT device 200 of the second embodiment do not synchronize with the collimator 8 but are disposed at fixed positions.

<<Modified Example of Second Embodiment>>

Figure 6:
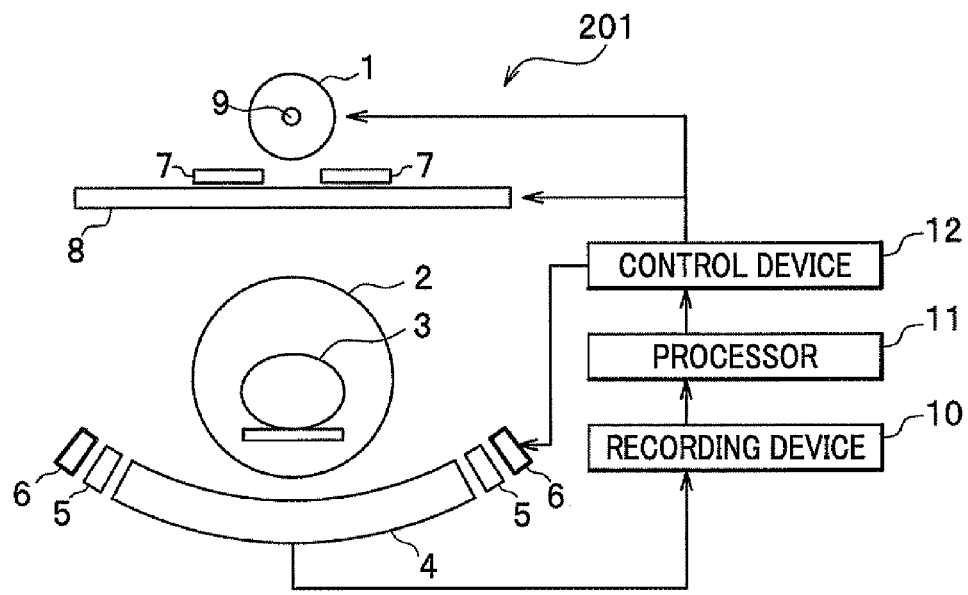
FIG. 6 is a diagram showing a configuration of an X-ray CT device according to a modified example of the second embodiment of the present invention as viewed from the body axis direction.
Figure 7:
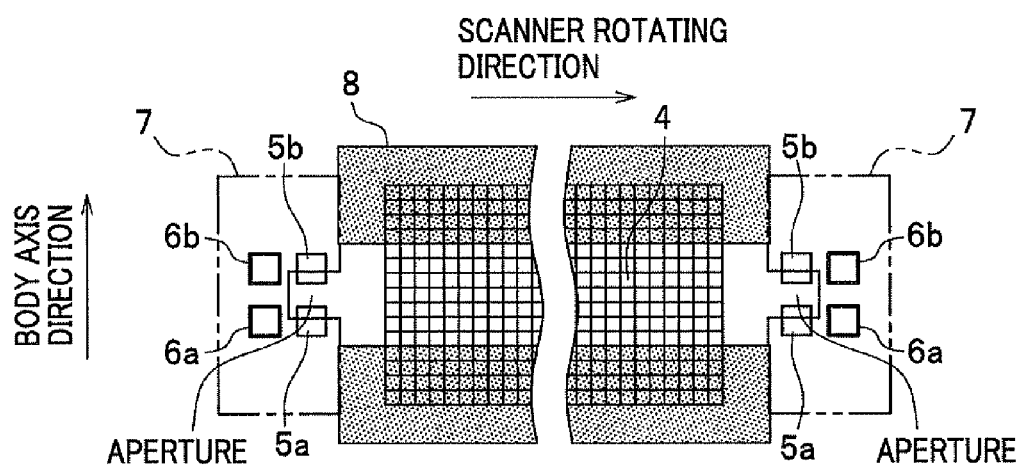
FIG. 7 is a diagram showing a configuration of the X-ray CT device according to the modified example of the second embodiment of the present invention as viewed from the X-ray beam irradiation direction.

FIGS. 6, 7, and 8 show an X-ray CT device 201 according to a modified example of the second embodiment of the present invention.

FIG. 6 is a diagram showing a configuration of the X-ray CT device according to the modified example of the second embodiment of the present invention as viewed from the body axis direction. FIG. 7 is a diagram showing a configuration of the X-ray CT device according to the modified example of the second embodiment of the present invention as viewed from the X-ray beam irradiation direction. FIG. 8 is a schematic diagram showing a general configuration of the X-ray CT device according to the modified example of the second embodiment of the present invention when the slit has a plurality of apertures.

According to the X-ray CT device 200 of the second embodiment, the scattered X-ray detector 6 is disposed in the body axis direction of the shift detector 5, while the scattered X-ray detector 6 may be disposed in the scanner rotating direction. The scattered X-ray detectors 6 may be disposed at both ends of the shift detector 5 in the scanner rotating direction. The other geometric arrangement and the flow of the data correction process are similar to those of the second embodiment. Here, FIGS. 3, 4, 5 may be observed in place of with FIGS. 6, 7, and 8, respectively. FIGS. 12 and 13 are common to this modified example. The wording of FIG. 15 may be read with reference to FIG. 7.

FIG. 9 shows a general configuration when the X-ray CT device in the second embodiment of the present invention and the X-ray CT device according to the modified example in the second embodiment of the present invention are combined together.

As shown in FIG. 9, the scattered X-ray detectors 6 may be disposed at the external ends of the shift detectors 5 in both body axis direction and scanner rotating direction in order to improve the estimation precision for the dose of scattered rays.

According to the X-ray CT device 201 of the modified example of the second embodiment, in addition to the (first advantage), (second advantage), (fourth advantage), and (fifth advantage) of the X-ray CT device 100 of the first embodiment and the (sixth advantage) and (seventh advantage) of the X-ray CT device 200 of the second embodiment, the following advantage can be further obtained.

(Eighth Advantage)

The penumbra area has no change in the scanner rotating direction even if the collimator 8 and the slits 7 are moved in the body axis direction. Hence, the shift detector 5 and the scattered X-ray detector 6 can be disposed so as to adjoin to each other, thereby minimizing the difference between the dose of scattered X-rays entering in the shift detector 5 and that of scattered X-rays entering in the scattered X-ray detector 6.

The X-ray CT device 200 of the second embodiment can obtain the following advantage relative to the X-ray CT device 201 of the modified example of the second embodiment.

(Ninth Advantage)

Arrangement of the shift detector 5 and the scattered X-ray detector 6 side by side in the body axis direction can make the arrangement of each detector compact.

<<Third Embodiment>>

The method of using the collimator 8 like the first embodiment and the method of providing the slits 7 like the second embodiment can be combined to carry out a method of forming a penumbra over the shift detector 5.

Detection of the positional shift of the X-ray focal point 9 and reference correction are both enabled through the following method using the same X-ray detector element row at the end of the main detector 4 in the scanner rotating direction.

Figure 16:
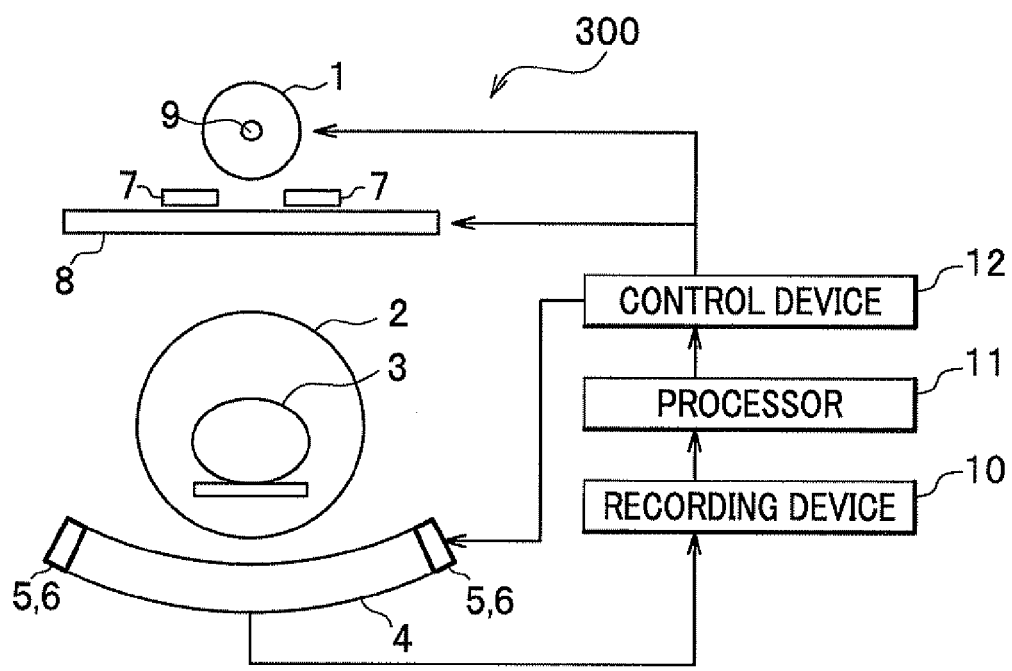
FIG. 16 is a diagram showing a configuration of an X-ray CT device according to a third embodiment of the present invention as viewed from the body axis direction.

FIGS. 16 and 17 show a geometrical arrangement of an X-ray CT device 300 according to a third embodiment of the present invention.

Figure 17A:
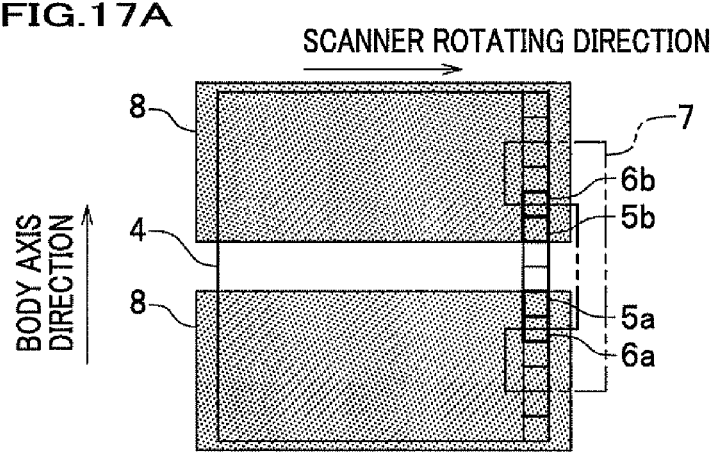
FIGS. 17A, 17B, and 17C are diagrams each showing a configuration of the X-ray CT device according to the third embodiment of the present invention as viewed from the X-ray beam irradiation direction, and showing cases that the respective widths of the collimator apertures are different.
Figure 17B:
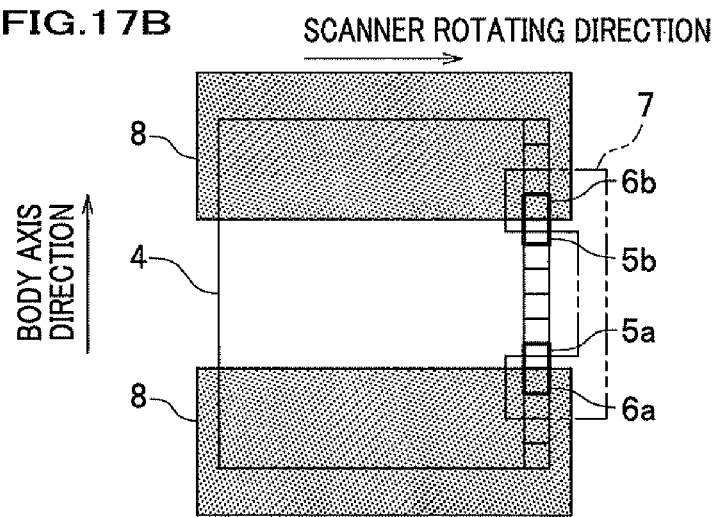
Figure 17C:
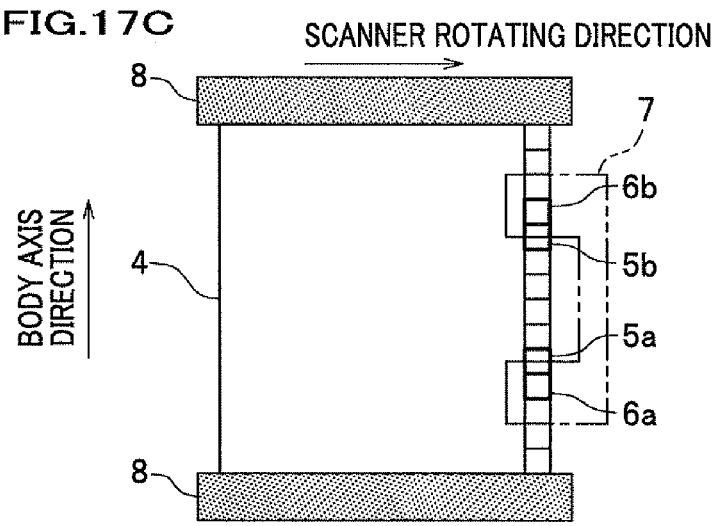

FIG. 16 is a diagram showing a configuration of the X-ray CT device according to the third embodiment of the present invention as viewed from a body axis direction. FIGS. 17A, 17B, and 17C are diagrams showing a configuration of the X-ray CT device according to the third embodiment of the present invention as viewed from an X-ray beam irradiation direction, and showing respective cases in which a collimator aperture width is different. The left (or the negative side of the scanner rotating direction) shift detector 5 and scattered X-ray detector 6 in FIGS. 17A, 17B, and 17C are omitted.

The basic configuration is identical to those of the first and second embodiments. However, like the first embodiment, the shift detectors 5 and the scattered X-ray detectors 6 are disposed at the ends of the main detector 4 in the scanner rotating direction as a part of the main detector 4, and the scattered X-ray detector 6 is disposed at the end of the shift detector 5 outwardly of the body axis direction.

Moreover, the X-ray detector elements serving as the shift detector 5 and the scattered X-ray detector 6 change depending on the aperture width of the collimator 8.

Next, will be explained an operation of the X-ray CT device 300 of the third embodiment when the aperture width of the collimator 8 is changed.

First, in the case of FIG. 17A in which the aperture width of the collimator 8 is narrower than the aperture width of the slit 7, the shift detector 5 is set in a region where the penumbra by the collimator 8 overlaps and the scattered X-ray detector 6 is set outside the penumbra region. That is, the positional shift of the X-ray focal point 9 is detected through the same method as that of the first embodiment. At this time, the reference data may be obtained without any problem since there are the X-ray detector elements irradiated with direct X-rays in all sliced rows. Moreover, regarding the sliced rows at the ends of the X-ray irradiation range, the gain change by the penumbra remains same at the main detector 4 that is the image pickup unit for the object 3 and at the end of the main detector 4 in the scanner rotating direction, and thus correction may be performed appropriately.

Next, in the case of FIG. 17C in which the aperture width of the collimator 8 is wider than the external width of the slit 7, the shift detector 5 is set in a region where the penumbra by the slit 7 overlaps and the scattered X-ray detector 6 is set outside the penumbra region. That is, the same method as that of the second embodiment is carried out.

The reference data may be obtained without any problem from the portion other than the portions shaded by the slit 7 and including the sliced row at the end of the X-ray irradiation range that has the largest sensitivity change. Regarding the sliced row shaded by the slit 7, data in the vicinity of the center where it can be estimated that no penumbra overlap is extrapolated to generate reference data. Alternatively, providing that the total of penumbra irradiation levels by the slit 7 (the total value of the outputs A and B detected by the shift detectors 5) do not change largely through the control for the collimator 8 even if the X-ray focal point 9 is shifted, reference correction is performed on the sliced row other than the end of X-ray irradiation range using the total data obtained from the elements other than the sliced row at the end of the X-ray irradiation range.

Finally, in the case of FIG. 17B in which the aperture width of the collimator 8 is wider than the aperture width of the slit 7 and is narrower than the external width thereof, the setting of the shift detector 5 and the scattered X-ray detector 6 maybe made as shown in FIG. 17B. However, the sensitivity change at the edge portion of the collimator 8 (the end in the X-ray irradiation range) having the largest sensitivity change is unobtainable. Hence, when it is also attempted to obtain reference data, the setting of the aperture width of the collimator 8 and that of the shape of the slit 7 used for imaging should be made so that the aperture width of the collimator 8 and the slit 7 do not have an arrangement shown in FIG. 17B. Alternatively, it is necessary to set the aperture width 8 slightly wide so that no penumbra overlap the imaging area.

Next, with reference to FIG. 18, an explanation will be given of a flow of a correction process for the positional shift of the X-ray focal point 9 and that of storing of the reference data.

Figure 18:
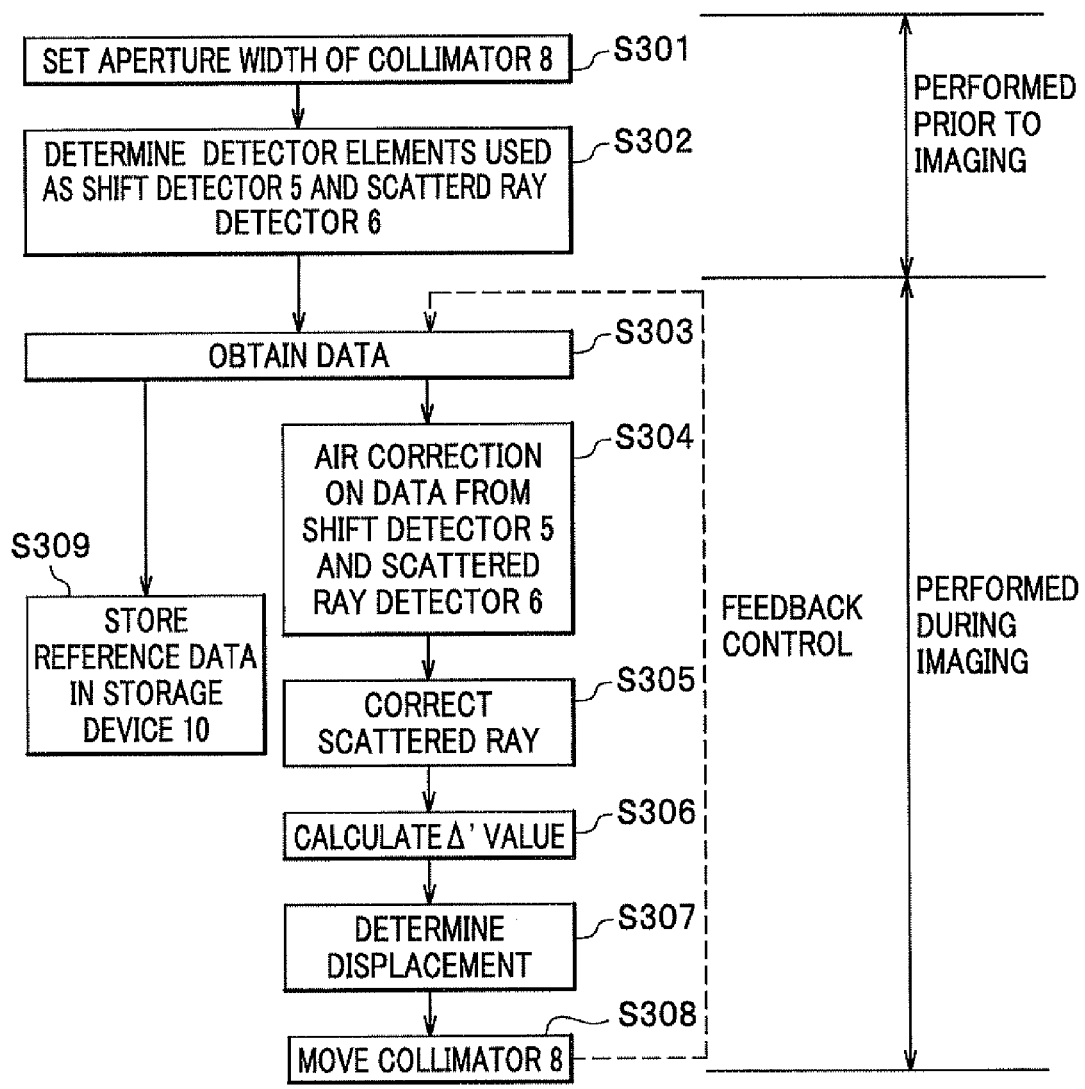
FIG. 18 is a flowchart showing a flow of a scattered ray correction process and a collimator control on the data output from a shift detector of the X-ray CT device according to the third embodiment of the present invention.

FIG. 18 is a flowchart showing a flow of a scattered ray correction process and a flow of a collimator control on data output by the shift detector of the X-ray CT device according to the third embodiment of the present invention.

The flow of the scattered ray correction process (step S305) and the collimator control process (step S308) according to the third embodiment are same as those of the first embodiment.

The basic flow is identical to that of the first embodiment, and FIGS. 16, 17A, 17B, 17C, and 18 may be observed in place of FIGS. 1, 2A, 2B, and 11, respectively.

Moreover, the steps S301, S302, S303, S304, S305, S306, S307, and S308 correspond to the steps S151, S152, S152, S154, S155, S156, S157, and S158, respectively.

However, the X-ray detector elements to be used as the shift detector 5 and the scattered X-ray detector 6 may be set (step S302) in accordance with a relationship between the aperture width of the collimator 8 and the slit 7 as explained above (see FIGS. 17A, 17B, and 17C).

Moreover, as shown in FIG. 18, a process (step S309) of storing pieces of data which are obtained from the shift detector 5 and the scattered X-ray detector 6 and which are to be used as reference data in the recording device 10 is added.

The control method of the collimator 8 using the information (Δ' value) on the shifting of the focal point (step S308) is identical to that of the second embodiment, and the slit 7 of the X-ray CT device 300 moves in synchronization with the control for the collimator 8 and is disposed in such a way that the aperture center of the slit 7 in the body axis direction always matches the aperture center of the collimator 8.

According to the X-ray CT device 300 of the third embodiment, in addition to the (first advantage), (second advantage), (third advantage), (fourth advantage), and (fifth advantage) of the X-ray CT device 100 of the first embodiment, the following advantages can be obtained.

(Tenth Advantage)

The reference data may be obtained simultaneously, and thus correction using the reference data is enabled. In particular, for the sliced X-ray element detector row at the end of the X-ray irradiation range adjusted by the collimator 8, reference correction may be performed appropriately.

(Eleventh Advantage)

The X-ray detector element can work for both of the reference correction and the detection of the focal point shifting, the arrangement may be made further compact, thereby reducing the cost.

(Twelfth Advantage)

Even if the aperture width of the collimator 8 is maximized, there are X-ray detector elements shaded by the slit 7, and thus the number of the unused X-ray detector elements may be minimized. That is, the sliced rows at the ends of the main detector 4 can be utilized maximally for imaging of the object 3.

| | Description of Reference Numerals |
|---|---|
| 1 | X-ray tube (X-ray source) |
| 2 | Opening |
| 3 | Object |
| 4 | X-ray detector for imaging object (main detector) |
| 5 | X-ray focal point shift detector (shift detector) (focal point shift detector) |
| 6 | Scattered X-ray detector (scattered ray detector) |
| 7 | Slit |
| 8 | Collimator |
| 9 | X-ray focal point |
| 10 | Recording device |
| 11 | Processor |
| 12 | Control device (moving mechanism) |

The invention claimed is:

1. An X-ray CT device comprising:
an X-ray source for emitting X-rays from an X-ray focal point;
a collimator for collimating the X-rays;
a main detector including a plurality of X-ray detector elements disposed in multiple rows to detect X-rays having penetrated an object;
a focal point shift detector for detecting a shift of the X-ray focal point; and
a scattered ray detector for measuring a dose of scattered rays entering the focal point shift detector.

2. The X-ray CT device according to claim 1, wherein the X-ray detector elements serving as the focal point shift detector and the scattered ray detector are determined in accordance with an aperture width of the collimator.

3. The X-ray CT device according to claim 1, further comprising a slit which forms a penumbra of the X-ray focal point over the focal point shift detector, and which also serves as a shield that prevents X-rays from directly entering in the scattered ray detector.

4. The X-ray CT device according to claim 3, wherein the slit is provided with a plurality of apertures.

5. The X-ray CT device according to claim 1, further comprising a slit which forms a penumbra of the X-ray focal point over the focal point shift detector and which also serves as a shield that prevents X-rays from directly entering in the scattered ray detector, wherein
the X-ray CT device simultaneously detects the positional shift of the X-ray focal point and reference correction by selecting the X-ray detector elements serving as the focal point shift detector from a region where X-rays directly enter; the region including the penumbra, and selecting the X-ray detector elements serving as the scattered ray detector from the outside of the region where the X-rays directly enter in accordance with an aperture width of the collimator.

6. The X-ray CT device according to claim 1, wherein the device uses measured data on different scanner rotating angles in order to estimate a dose of scattered rays entering in the focal point shift detector.

7. The X-ray CT device according to claim 1, further comprising a unit for detecting a presence of the object between the focal point shift detector and the X-ray focal point and determining whether the collimator needs to be controlled or not.

8. An X-ray CT device comprising:
  an X-ray source for emitting X-rays from an X-ray focal point;
  a collimator for collimating the X-rays;
  a main detector including a plurality of X-ray detector elements disposed in multiple rows to detect X-rays having penetrated an object;
  a focal point shift detector for detecting shift of the X-ray focal point; and
  a scattered ray detector for measuring a dose of scattered rays entering in the focal point shift detector, wherein
  the X-ray CT device controls a range of emitted X-rays entering in the main detector based on data detected by the focal point shift detector and data detected by the scattered ray detector.

9. The X-ray CT device according to claim 8, wherein the range of the emitted X-rays is controlled by a moving mechanism that moves the collimator.

10. The X-ray CT device according to claim 8, wherein the range of the emitted X-rays is controlled by a moving mechanism that moves the X-ray focal point.

11. The X-ray CT device according to claim 8, wherein the range of the emitted X-rays is controlled through a negative feedback control.

12. A method for an X-ray CT device comprising functions of:
  emitting X-rays from an X-ray focal point;
  collimating the X-rays;
  detecting X-rays having penetrated an object;
  detecting shift of the X-ray focal point; and
  measuring a dose of scattered rays included in output data through the function of detecting shift of the X-ray focal point, wherein
  the X-ray CT device corrects a dose of scattered rays in the output data through the function of measuring the dose of scattered rays when the function of detecting shift of the X-ray focal point calculates a shift distance of the X-ray focal point.

* * * * *